(12) United States Patent
Mintchev et al.

(10) Patent No.: US 9,084,663 B2
(45) Date of Patent: Jul. 21, 2015

(54) ELECTRONIC DEVICE FOR WEIGHT CONTROL

(71) Applicant: EatLittle Inc., Calgary (CA)

(72) Inventors: Martin Pavlov Mintchev, Calgary (CA); Orly Yadid-Pecht, Calgary (CA)

(73) Assignee: Eat Little Inc., Calgary, Alberta (CA)

( * ) Notice: Subject to any disclaimer, the term of this patent is extended or adjusted under 35 U.S.C. 154(b) by 0 days.

(21) Appl. No.: 14/176,802

(22) Filed: Feb. 10, 2014

(65) Prior Publication Data

US 2014/0188154 A1  Jul. 3, 2014

Related U.S. Application Data

(62) Division of application No. 11/718,514, filed as application No. PCT/CA2005/001693 on Nov. 4, 2005, now Pat. No. 8,691,269.

(60) Provisional application No. 60/666,517, filed on Mar. 22, 2005, provisional application No. 60/625,093, filed on Nov. 5, 2004.

(51) Int. Cl.
*A61F 5/00* (2006.01)

(52) U.S. Cl.
CPC .................................... *A61F 5/0036* (2013.01)

(58) Field of Classification Search
None
See application file for complete search history.

(56) References Cited

U.S. PATENT DOCUMENTS 7,066,945 B2 *   6/2006   Hashiba et al. ............... 606/191
2005/0222537 A1 * 10/2005   Dinsmoor et al. ............ 604/174

FOREIGN PATENT DOCUMENTS

WO         2004/056343      *  7/2004

OTHER PUBLICATIONS

Schenning (Schenning, Jessica A., "Hydraulic performance of polymer modified bentonite" (2004). Theses and Dissertations. Paper 1238. http://scholarcom mons.usf.edu/etd/1238).*

* cited by examiner

*Primary Examiner* — Suzanne Ziska
(74) *Attorney, Agent, or Firm* — Kyle R. Satterthwaite; Ryan W. Dupuis; Ade & Company Inc.

(57) ABSTRACT

Orally administrable polymer-carrying units for expanding in a stomach of a mammal to fill a space in the stomach, the polymer-carrying units including: a carrier; a plurality of polymer molecules expandable in aqueous solutions, releasably coupled to the carrier; and means for selectively decoupling the polymer molecules from the carrier so that the polymer molecules and carrier are released in the stomach, are provided.

17 Claims, 19 Drawing Sheets

ELECTRONIC DEVICE FOR WEIGHT CONTROL

CROSS REFERENCE TO RELATED APPLICATION(S)

This application is a divisional of U.S. Ser. No. 11/718,514, which entered the national stage on Nov. 6, 2007 on the basis of International PCT application Ser. No. PCT/CA2005/001693 filed on Nov. 4, 2005, and which claimed benefit under 35 U.S.C. §1.19(e) of U.S. Ser. No. 60/625,092 filed Nov. 5, 2004, and U.S. Ser. No. 60/666,517, filed Mar. 22, 2005, the entire contents of which are incorporated herein by reference.

FIELD OF THE INVENTION

The present invention relates to the field of ingestible microelectronic dosage forms, and more specifically to ingestible, electronically-controlled and timed dosage forms comprising expandable polymeric material useful for weight control and the treatment of obesity.

BACKGROUND OF THE INVENTION

Weight control and treatments for obesity have been the subjects of a large amount of suggested diets, treatments and procedures, including, in the most severe cases of morbid obesity, device implantations and/or direct surgical interventions. Recent comprehensive statistics from the National Institutes of Health (USA) indicates that more that 40% of Americans are obese, with more than 20% of these individuals being morbidly obese. In addition, it can be estimated that at least twice as many people are seeking to control their body weight, and/or are adhering to diets or other weight-control mechanisms. This is particularly significant since obesity has been implicated as a leading cause of various clinical conditions, including cardiovascular diseases and diabetes.

Six major streams of research and development related to new treatments for obesity are currently available: (1) diet regiments, and diet-related supplements and treatments; (2) pharmacological treatment using specifically developed medications; (3) gastric stimulation using implantable electronic devices; (4) invasive surgical procedures related to gastric reduction; (5) intragastric balloons for reducing gastric volume and introducing a sensation of satiety and fullness; and (6) oral administration of cellulose or polymeric-based substances, which expand in the stomach and preclude their expulsion through the pylorus with the process of natural gastric peristalsis, thus introducing sensation of fullness and satiety. These expanded polymeric substances subsequently disintegrate chemically to allow for their expulsion from the body with natural gastrointestinal peristalsis.

Currently, there are very large numbers of various diets, diet supplements, diet regimens, and combinations thereof, and their numbers are growing dramatically. However, in many cases, these weight loss strategies do not work, or their success is very limited. The success of these techniques often varies widely between individuals, and they are often not sustainable.

Weight-loss related pharmacological treatment based on specifically developed and clinically-tested drugs and/or health supplements has also not been very successful. Numerous such therapies have been associated with various side effects, some of which are quite serious and life-threatening. Therefore, commercially-available and clinically-proven diets and/or anti-obesity drugs and health supplements have yet to be developed.

Recently developed techniques for gastric stimulation (see for examples U.S. Pat. Nos. 6,684,104, 6,615,084, 6,606,523, 6,600,953, 6,542,776, 6,535,764, and 6,449,511), involving surgical implantation of miniature microelectronic devices have been proposed as an avenue to tackle more severe cases of obesity, and particularly morbid obesity. The devices can administer electrical signals to the stomach and adversely affect normal propulsive gastric peristalsis. However, the procedures used for the positioning of the electrode as well as the implantation of the device remain invasive, and the long-term effect of the treatment remains unknown both in terms of sustainability and safety.

Surgical procedures related to gastric volume reduction are invasive measures to address the problem of obesity. Mortality rates of procedures like gastric bypass or direct gastric volume reduction can reach 2%, have prolonged recovery periods, and can be quite expensive.

Intragastric balloons or devices positioned in the stomach either surgically or endoscopically to reduce the effective gastric volume have been found effective in introducing early satiety and sensation of fullness, thus contributing to reduced food intake, which has been reliably related to sustainable weight loss (see for example U.S. Pat. Nos. 4,739,758, 4,485,805, 4,899,747, 5,234,454, 5,993,473, and 6,579,301). More recently, wireless control of volume-controlling devices in the stomach has been suggested (see for example U.S. Pat. Nos. 6,461,293, 6,454,699, 6,453,907, 6,460,543, and 6,450,946). However, these techniques remain invasive and can be associated with serious and sometimes life-threatening side-effects.

Most recently, the use of swellable polymers has been proposed to facilitate the reduction of gastric volume for treating obesity (see for example U.S. Pat. Nos. 5,750,585, 6,271,278, German Pat. No. NDN-050003290517, and US Patent Application No. 20040192582). Compressed cellulose derivatives, or dehydrated hydrophilic polymers are introduced orally in the stomach, and expand to the point of not being able to pass through the pylorus, thus effectively achieving non-invasively what an intragastric balloon or another gastric volume-reducing device would achieve. However, the subsequent decomposition and/or degradation of these polymers to allow for expulsion through natural peristalsis can be very problematic. More specifically, the decomposition and/or degradation rate is not precisely controlled, and the volume and the number of the decomposing/degrading parts or portions is unknown. More importantly, since this decomposition is pharmacologically-based, its timing cannot be precisely controlled since it would depend on numerous external factors related to the gastric pH, enzyme content, peristaltic pattern, and the anatomy of the particular patient. Because of the uncontrolled nature of the decomposition, it is possible that the volume of the stomach may remain in an expanded state for long intervals of time, which can lead to serious side-effects and significant discomfort. Moreover, improper decomposition and/or degradation may lead to serious complications such as small bowel obstructions.

Consequently, the need has arisen for non-invasive techniques or products that can be easily used for prolonged and controlled reduction of gastric volume for use in facilitating weight loss, which address some of the problems encountered in the prior art.

SUMMARY OF THE INVENTION

According to a broad aspect of this invention, there is provided an orally administrable polymer-carrying unit for expanding in a stomach of a mammal to fill a space in the stomach, the polymer-carrying unit including: a carrier; a plurality of polymer molecules expandable in aqueous solutions, releasably coupled to the carrier; and means for selectively decoupling the polymer molecules from the carrier so that the polymer molecules and carrier are released in the stomach.

The decoupling means can include a timer programmable to decouple the polymer molecules at selected intervals of time, resulting in a precisely timed, electronically controlled release of the polymer molecules. Moreover, the timer can be activated to decouple the polymer molecules when desired by using, for example, an external radio-frequency (RF) transmitter. In this embodiment, the decoupling means further comprises a miniature RF receiver. The timer and miniature RF receiver are both operably associated with the carrier. In one embodiment, the carrier has an internal cavity for housing the timer and RF receiver. In a further embodiment, the decoupling means further comprises a battery that may also be housed in the internal cavity of the carrier.

The polymer molecules can be selected from a large variety of different polymers, and can include a mixture of natural clay and/or various types of biocompatible polymers, for example, which is not meant to be limiting, superabsorbent and filler material such as Bentonite, microcrystalline hydrogels and polyolefins. Further, if desired, the polymer molecules can be biodegradable to facilitate the release of the carrier and polymer molecules from the stomach. The polymer-carrying unit may also further include at least one active agent, which can be releasably associated with either the carrier or the polymer molecules, or both. The active agent may be selected from a wide group of agents, which include, but are not limited to, enzymatic agents, medicinal agents, chemical agents, or combinations thereof. The polymer molecules may be releasably coupled to the carrier by means of electric forces, magnetic forces, electrostatic forces, electromagnetic forces, frictional forces, a fiber, or piezoelectric hinges.

According to another broad aspect of this invention, there is provided an orally administrable polymer-carrying unit for expanding in a stomach of a mammal to fill a space in the stomach, the polymer-carrying unit including: a carrier having at least one outer surface; at least one coupling member having a first surface and a second surface; a plurality of polymer molecules expandable in the presence of an aqueous solution associated with the first surface of the coupling member; a coupling means for releasably coupling the second surface of the coupling member to the outer surface of the carrier; and a decoupling means for selectively decoupling the carrier from the coupling member.

The carrier may adopt a wide variety of different shapes, which can include, but are not limited to, sphere-like, triangular-like, pyramid-like, and cube-like shapes. Moreover, the coupling means can be selected from, but are not limited to, an electromagnetic force, a frictional force, piezoelectric hinges, or combinations thereof. The decoupling means, which may be operably associated with the carrier, can also be quite diverse, and can comprise a timer, a battery, a radio-frequency receiver, or combinations thereof. In one embodiment, the carrier comprises an internal cavity and the decoupling means comprises an electronic device selected from the group consisting of a timer, a battery, a radio-frequency receiver, or combinations thereof, housed within the internal cavity. In one embodiment, the coupling means can be a frictional force and the decoupling means can be an electromagnet operatively associated with the outer surface of the carrier and means for activating the electromagnet to create a magnetic field. In this embodiment, the coupling member can include a material that can be repelled by the magnetic field. In another embodiment, the coupling means can be a piezoelectric hinge and the decoupling means can produce an electric voltage to control motion of the piezoelectric hinge.

As mentioned, the polymer molecules can be a mixture of Bentonite and/or a biocompatible polymer, and can be biodegradable. The polymer-carrying unit may also further include at least one active agent, which can be releasably associated with either the carrier or the polymer molecules, or both. The active agent may be selected from a wide group of agents, which include, but are not limited to, enzymatic agents, medicinal agents, chemical agents, or combinations thereof.

According to another broad aspect of this invention, there is provided an arrangement of polymer-carrying units, the arrangement comprising a first unit and a second unit, wherein the outer surface of the first unit is releasably coupled to the outer surface of the second unit by means of electric forces, magnetic forces, electrostatic forces, electromagnetic forces, or a combination thereof.

According to another broad aspect of this invention, there is provided an orally administrable dosage form, the dosage form comprising: one or more polymer-carrying unit or an arrangement of polymer-carrying units and at least one pharmaceutically acceptable excipient. The dosage form may be a capsule, which can be coated with a pH-sensitive coating layer. The pH-sensitive coating layer can be formulated to prevent dissolution prior to the dosage form reaching the stomach.

According to another broad aspect of this invention, there is provided an orally administrable polymer-carrying unit comprising: a carrier having an outer surface and an inner surface, the inner surface forming an internal cavity; at least one fiber for releasably supporting a plurality of sacs, the sacs containing polymer molecules, the fiber being threaded into or through the internal cavity of the carrier so that at least one segment of the fiber is located within the internal cavity; a decoupling means located in the internal cavity for decoupling the sacs from the carrier by cutting the internal segment of the fiber so that the sacs are released from the carrier. In one embodiment, the decoupling means comprises an electrical wire located in the internal cavity of the carrier, the electrical wire being heated when desired to melt and cut the internal segment of the fiber. The polymer molecules can be a mixture of Bentonite and/or various types of biocompatible polymers, for example, which is not meant to be limiting, super-absorbent and filler material such as microcrystalline, hydrogels and polyolefins. The polymer molecules can also be biodegradable.

According to another broad aspect of this invention, there is provided a method for the non-invasive reduction of gastric volume, the method comprising the steps of: (a) orally administering at least one polymer-carrying unit as described above; (b) contacting the polymeric-carrying unit with gastric juice to allow for the polymer molecules to expand and prevent the polymer-carrying unit from exiting the stomach; and (c) after a desired period of time selectively decoupling the polymer molecules from the unit so that exit from the stomach is permitted.

BRIEF DESCRIPTION OF THE DRAWINGS

The present invention, both as to its organization and manner of operation, may best be understood by reference to the following description, and the accompanying drawings of various embodiments wherein like reference numerals are used throughout the several views, and in which.

DESCRIPTION OF THE PREFERRED EMBODIMENTS

An orally administrable polymer-carrying unit for expanding in a stomach of a mammal to fill a space in the stomach, as described herein, includes at least a carrier; a plurality of polymer molecules expandable in aqueous solutions that are releasably coupled to the carrier; and means for selectively decoupling the polymer molecules from the carrier so that the polymer molecules and carrier are released in the stomach. When the polymer-carrying unit expands in the stomach, the expanded size of the unit is such that passage of the unit through the pylorus is prevented, which can result in the attainment of a sensation of satiety for a specified period of time when the stomach remains filled with the unit.

After a desired amount of time has passed, the decoupling means can be activated in a timed and controlled manner to allow for the disintegration of the polymer-carrying unit by selectively releasing the polymer molecules from the carrier. This disintegration can allow the disintegrated parts of the unit to now pass through the pylorus, and empty from the stomach. The decoupling means can vary widely and can either be pre-programmed before ingestion or programmed after ingestion. Thus, only certain sections of the polymer-carrying unit can be allowed to disintegrate at one time. This can be particularly useful for the facilitation of weight loss and the treatment of obesity. The polymer-carrying unit can be a non-invasive treatment for obesity that can be timed and controlled, which can result in less discomfort to the subject ingesting the unit.

Figure 1:
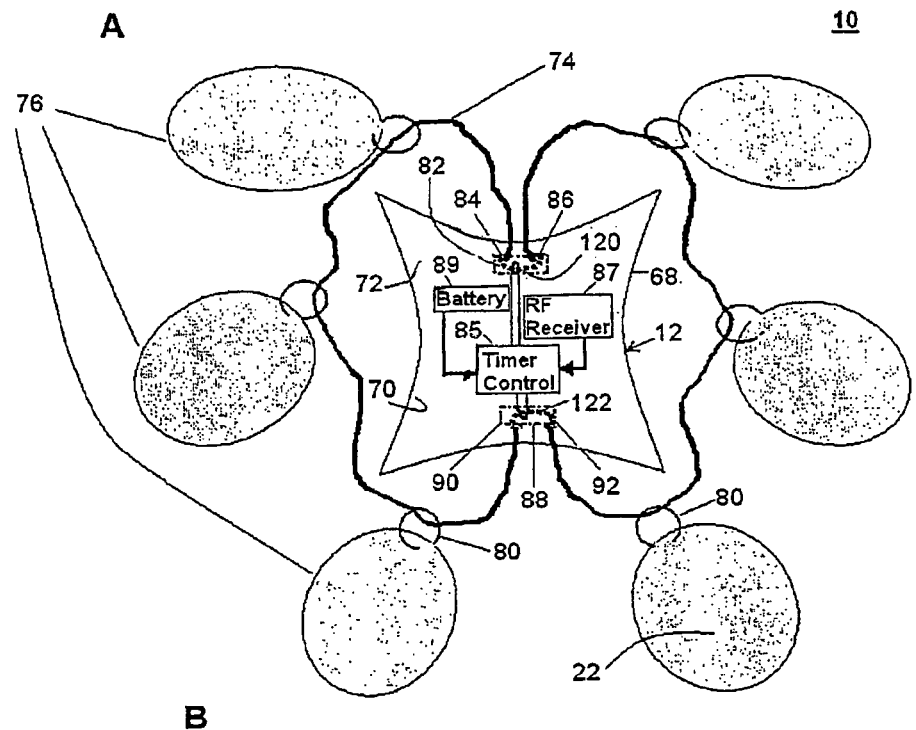
FIG. 1A is a schematic view of one embodiment of a polymer-carrying unit according to the invention, with the polymer molecules and sacs in an expanded state.
FIG. 1B is a schematic view of the polymer-carrying unit of FIG. 1A in an encapsulated state.
Figure 1:
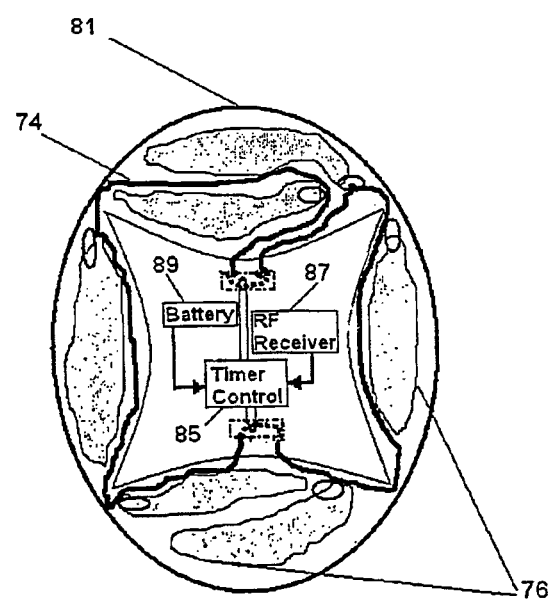
Figure 2:
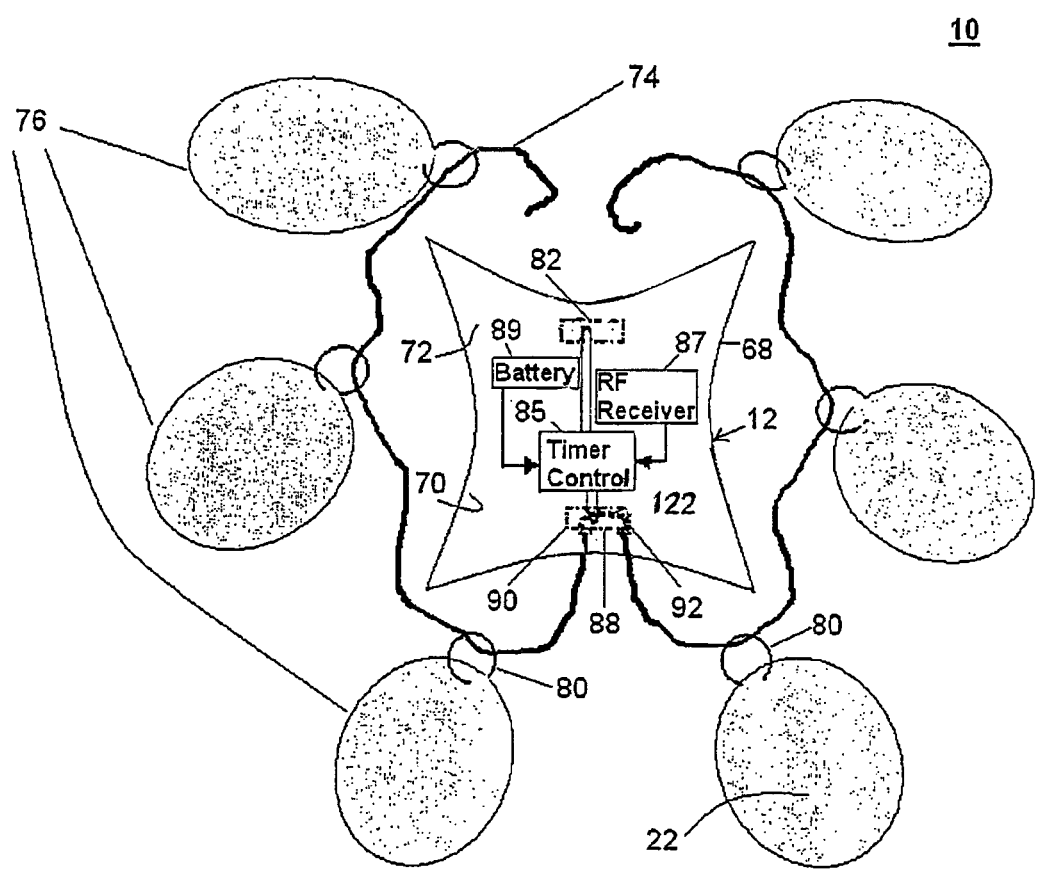
FIG. 2 is a schematic view of the polymer-carrying unit of FIG. 1A, where the fiber has one cut.
Figure 3:
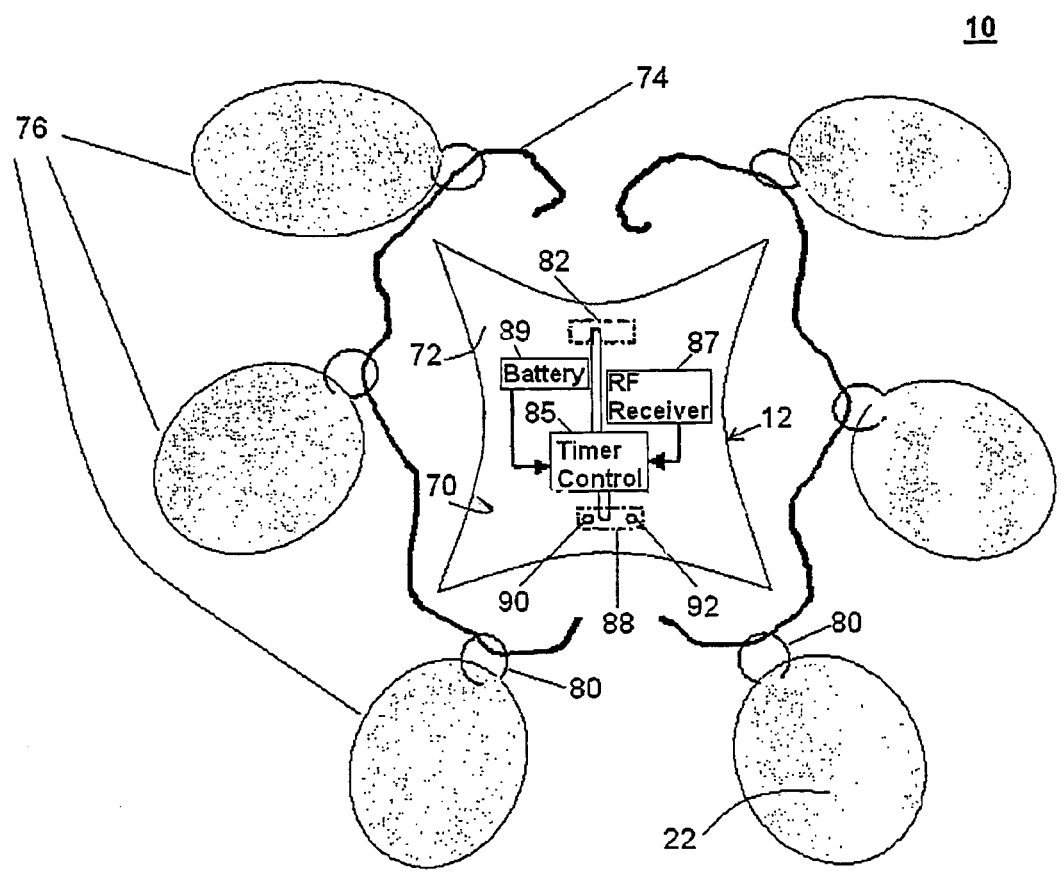
FIG. 3 is a schematic view of the polymer-carrying unit of FIG. 1A, where the fiber has two cuts.
Figure 4:
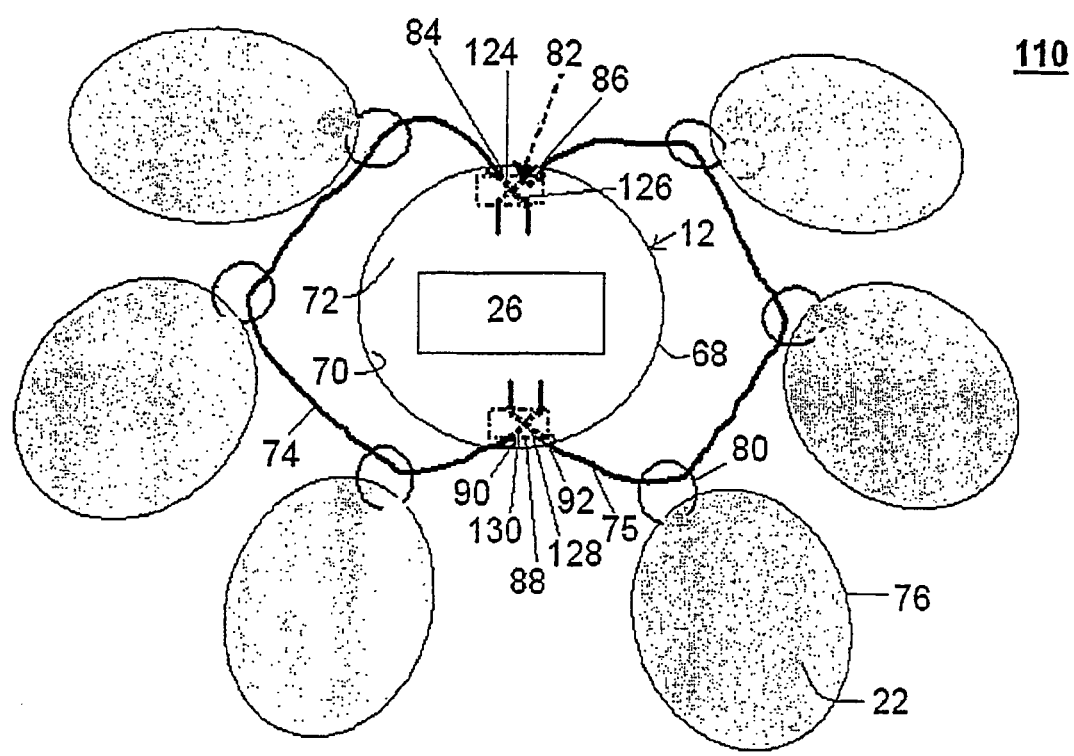
FIG. 4 is a schematic view of another embodiment of a polymer-carrying unit according to the invention having two fibers.
Figure 5:
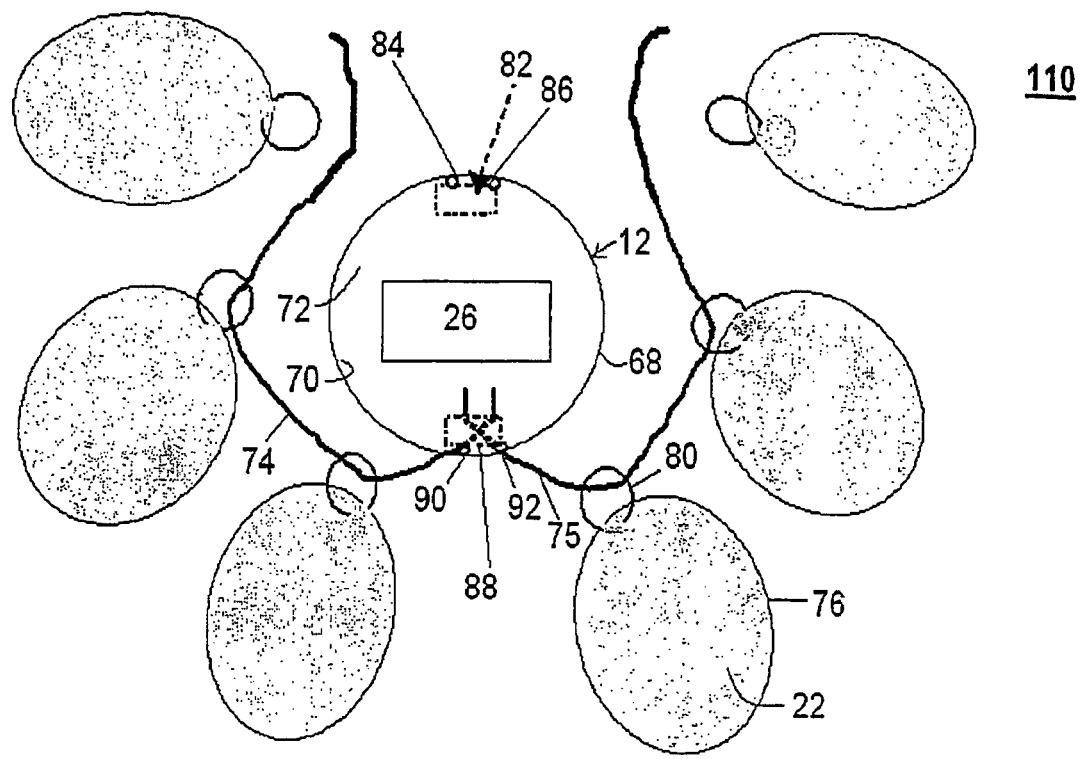
FIG. 5 is a schematic view of the polymer-carrying unit of FIG. 4, where each of the fibers have one cut.
Figure 6:
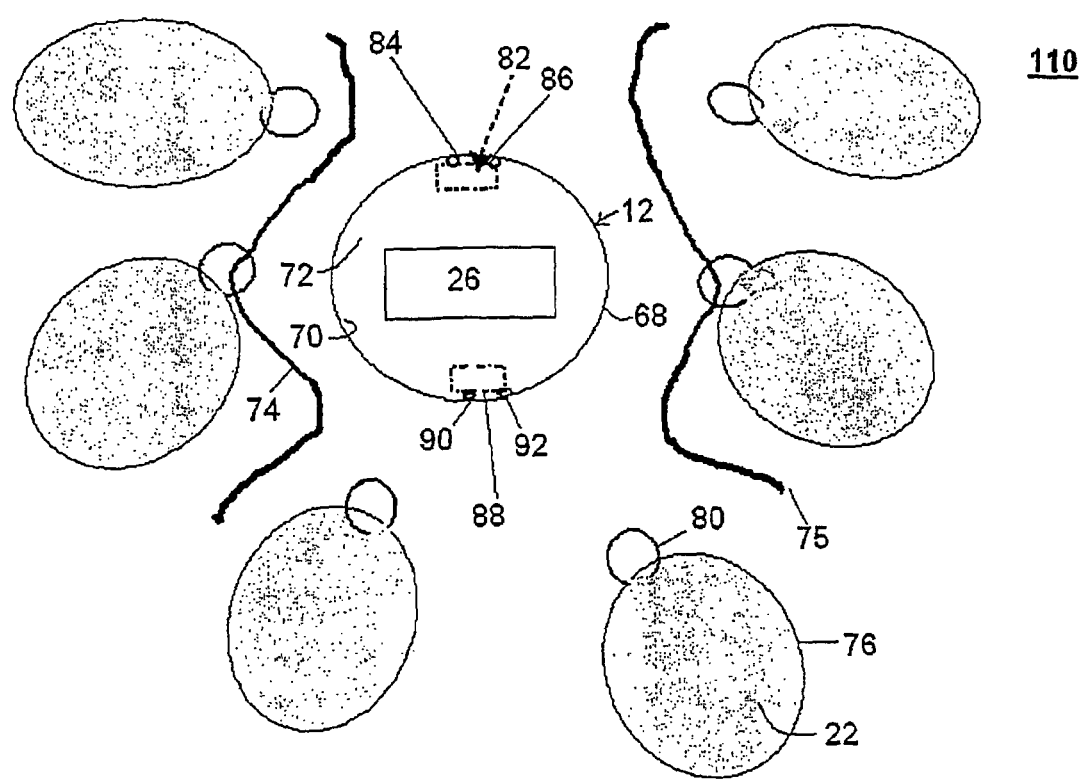
FIG. 6 is a schematic view of the polymer-carrying unit of FIG. 4, where each of the fibers have two cuts.

In the embodiment as illustrated in FIGS. 1-3 and the embodiment as illustrated in FIGS. 4-6, the polymer-carrying unit, referred to generally as element 10 and 110, respectively, includes a carrier 12 having an outer surface 68 and an inner surface 70, with the inner surface forming an internal cavity 72. In this embodiment, polymer molecules 22 are carried in a plurality of sacs 76 that are releasably coupled to the carrier 12 by at least one fiber 74. The decoupling means 26 for selectively decoupling polymer-containing sacs 76 is located in internal cavity 72 and operates to cut fiber 74 to release the sacs. Desirably, fiber 74 is arranged so as to maximize coverage of carrier 12 with sacs 76. If desired, sacs 76 can be supported by fiber 74 through rings 80, as shown in FIGS. 1-6.

In the embodiment illustrated in FIGS. 1-3, fiber 74 can be threaded through internal cavity 72 of the carrier to form a closed loop so that at least one segment of fiber 74 is located within the internal cavity. Fiber 74 can enter carrier 12 at first location 82 through apertures 84 and 86, forming an internal fiber segment 120, and also at second location 88, through apertures 90 and 92, forming internal fiber segment 122. Of course, if desired, more than two locations can also be used.

Figure 13:
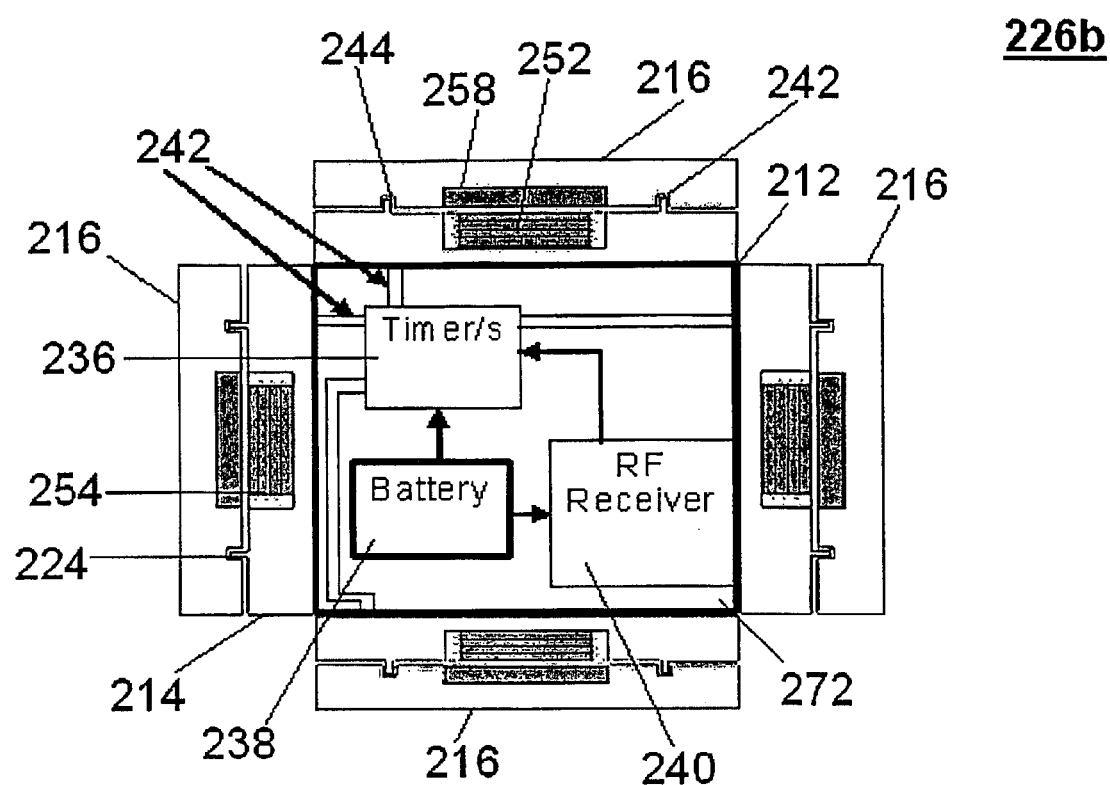
FIG. 13 is a schematic view of one embodiment of a decoupling means according to the invention.

In the embodiment illustrated in FIGS. 4-6, at least two fibers 74, 75 can be connected to carrier 12. As shown in FIG. 13, one fiber 75 can be connected to carrier 12 at aperture 86 of first location 82, and aperture 92 of second location 88, while the other fiber 74 can be connected to carrier 12 at aperture 84 of first location 82 and aperture 90 of second location 88. In this manner, both fibers 74, 75 can have a segment 124, 126, 128, 130 located within internal cavity 72, which may facilitate cutting, as will be discussed below.

In the embodiments illustrated in FIGS. 1-6, polymer molecules 22 can include any polymer that can expand when in contact with aqueous solutions, and can include, but are not limited to, natural clays (for example, which is not meant to be limiting, Bentonite), microcrystalline hydrogels, polyolefins, polyvinyl alcohol, poly(ethyloxazoline), polyvinylacetate-polyvinylalcohol copolymers, poly(2-hydroxyethylacrylate), poly(2-hydroxyethylmethacrylate), polyacrylic acid, and copolymers thereof, polysaccharides, water soluble proteins, polynucleic acids, or a combination thereof. Polymer molecules 22 can be made, if desired, of polyacrylic acid and a crosslinker by solution or suspension polymerization, using the type and quantity of crosslinker to control the swelling capacity and the gel modulus. The synthesis and use of such polymer molecules have been previously described in the following references, incorporated herein by reference: (1) Buchholz and Peppas, Superabsorbent Polymers, ACS Symposium Series, 1994; (2) Buchholz and Graham, Modern Superabsorbent Polymer Technology, John Wiley & Sons, 1998; and (3) Biocompatible/Biodegradable Materials (Tutorial). Sigma-Aldrich, 2005, available online at: http://www.sigmaaldrich.com/Area of Interest/Chemistry/MaterialsScience/BiocompatibleBiodegradable/Tutorial.html.

Sacs 76 can be made of an expandable permeable liner. The permeable liner should be able to allow aqueous solutions to enter sacs 76 and contact polymer molecules 22 to allow for their expansion. In one embodiment, sacs 76 can be made from natural cellulose fiber or specialty fiber through spun laced process, spun-bonded polypropylene or absorbable haemostatic oxidised regenerated cellulose (commercially available under the name Curasel), and are initially folded, containing the non-expanded polymer molecules. It may be desirable that the material used to construct sacs 76 be expandable, so as to concurrently expand with polymer molecules 22. As a safety feature, sacs 76 may be made of biodegradable material, so as to allow for biodegradation after several days. Moreover, fiber 74, 75 and rings 80 can also be made of a biocompatible material, which can include, but are not limited to, P-767, Azdel fiber or unreinforced Nylon 612. However, it may be desirable to select a material for fiber 74, 75 capable of withstanding the maximum peristaltic force present in the stomach to prevent release of sacs 76.

Decoupling means 26, which can be located within internal cavity 72, can be used to cut an internal segment of fibers 74 and/or 75 to decouple or release sacs 76 when exit from the stomach is desirable. As shown in FIGS. 2, 3, 5 and 6, fibers 74 and/or 75 can be cut either at one location or at more than one location. Of course, additional cuts can also be made if desired. One way of cutting can be melting the internal segment of the fiber. Once fibers 74 and/or 75 is/are cut, sacs 76 can become separated from polymer-carrying unit 10.

Figure 7:
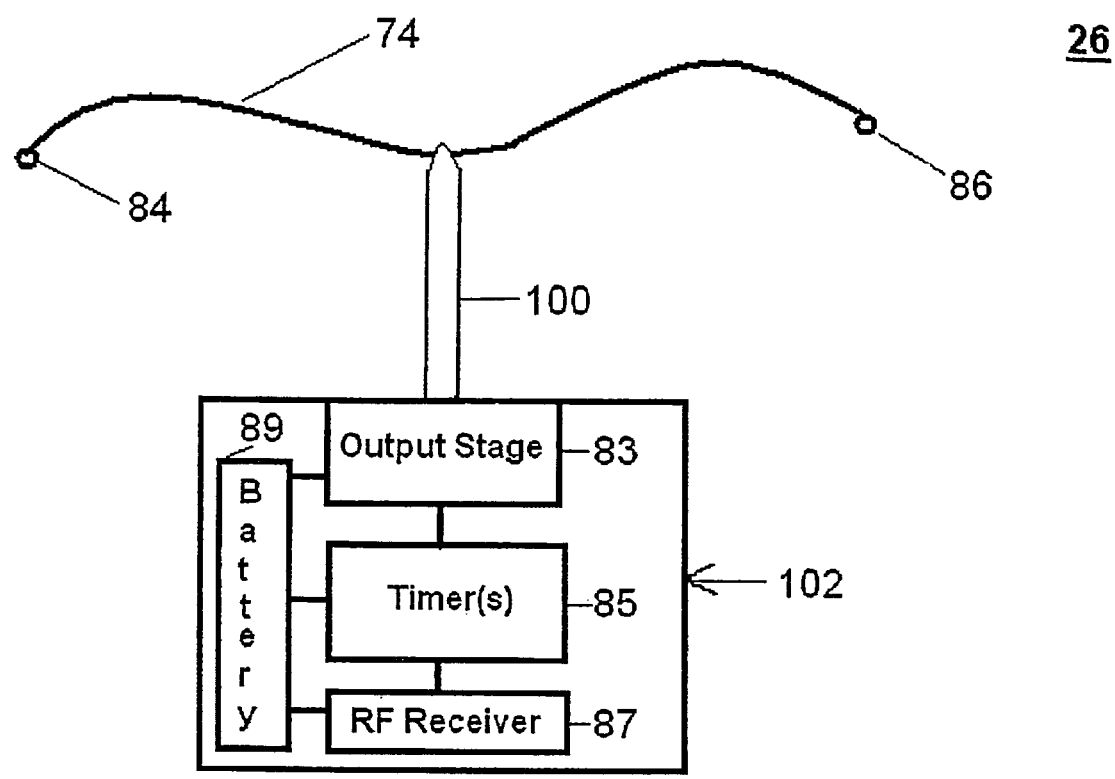
FIG. 7 is a schematic view of one embodiment of a decoupling means according to the invention.

Decoupling means 26 can take a variety of different forms. In the embodiment illustrated in FIG. 7, decoupling means 26 can include an electrical wire 100. When appropriate electric current flows through wire 100, its temperature in the area where it contacts fibers 74 and/or 75 increases, and the fiber(s) melts. Fibers 74 and/or 75 is/are preferably comprised of a material having a low melting point. In one embodiment, fibers 74 and/or 75 can have a melting point of about 45° C. to about 180° C., for example, P-767, Azdel fiber or unreinforced Nylon 612. An electronically-controlled microheater 102 can be used to provide electrical wire 100 with the required energy to cut fiber 74. In one embodiment, microheater 102 can generate sufficient energy to raise the temperature of electrical wire 100 to about 10° C. above the melting point of fiber 74, by allowing an impulse current of appropriate magnitude to flow through the wire. Wire 100 can be connected to an output electronic stage 83, which can be controlled by at least one timer 85 (as shown in FIG. 7). An RF receiver 87 and battery 89 can also be used to control wire 100 in a timed and controlled manner. The timer(s), which can be pre-programmed, or can be controlled by the RF receiver, can be coupled to an electronic output stage designed with standard power transistors, which can deliver the necessary current to the electrical wire, so that the microheater increases its temperature above the melting point of the fiber, holding the sacs containing the expanded polymer molecules. For example, which is not meant to be limiting, fiber 74 can be cut at several locations, wherein each cut is performed over a certain period of time to allow for partial disintegration, or in embodiments including more than one fiber, i.e., fibers 74, 75, only one fiber may cut at a certain time. If desired, separate electronic devices may be used for each fiber 74, 75, or for each cut.

Figure 18:
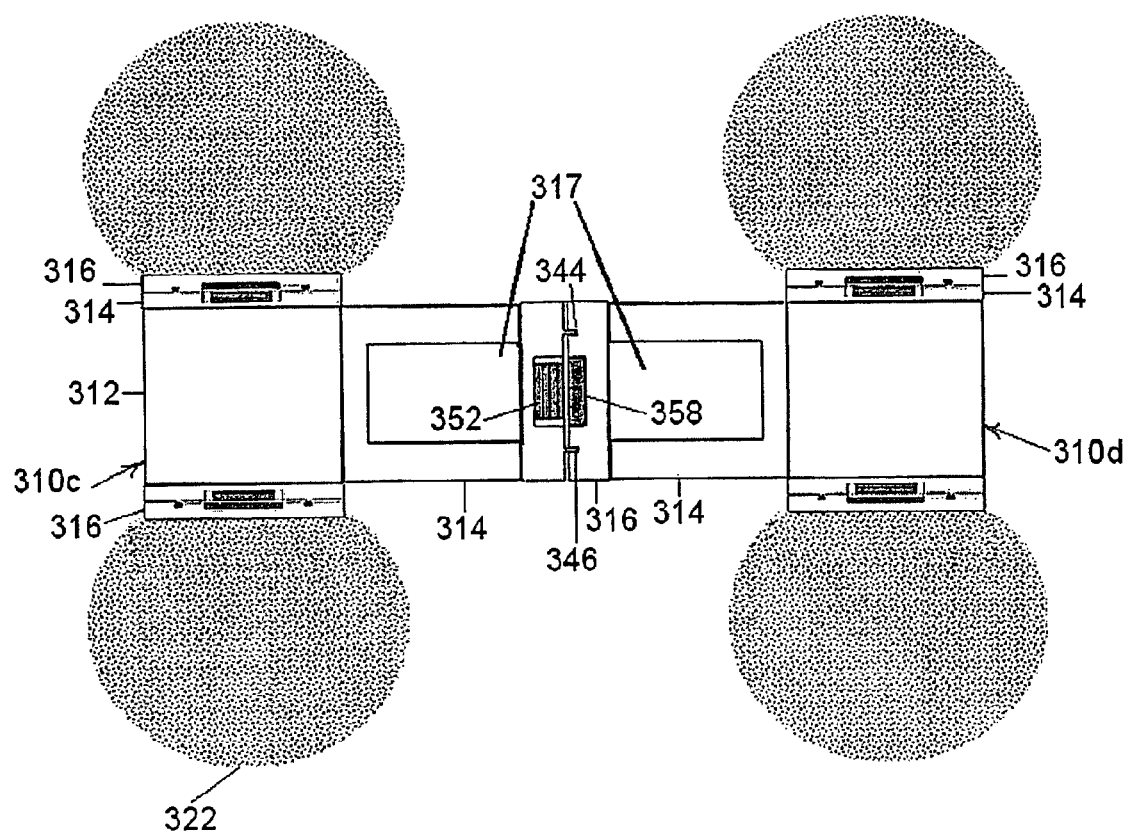
FIG. 18 is a schematic view of one embodiment of an arrangement of polymer-carrying units according to the invention.

In the embodiment illustrated in FIG. 18, polymer-carrying unit 10 can be contained within a shell 81, with sacs 76 in a folded conformation to facilitate oral administration. Shell 81 can be made of a variety of different materials, which can include, but are not limited to, pH-sensitive materials that will only dissolve under certain conditions, for example, the pH of the stomach. The material used to make the shell can be the same material, for example, gelatine or cellulose, used to make pharmaceutical capsules known in the art. Various sizes of shells can be used, as long as they are swallowable by the patient.

Figure 8:
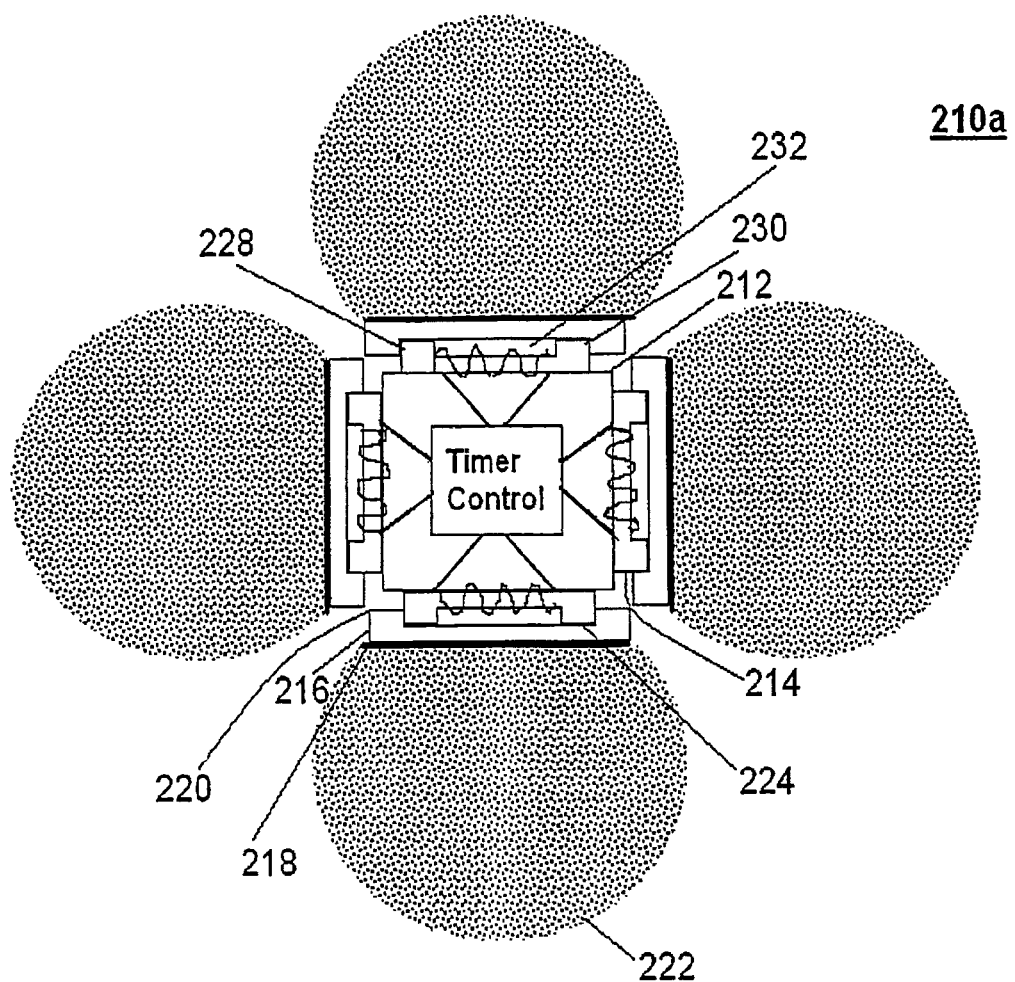
FIG. 8 is a schematic view of another embodiment of a polymer-carrying unit according to the invention.
Figure 9:
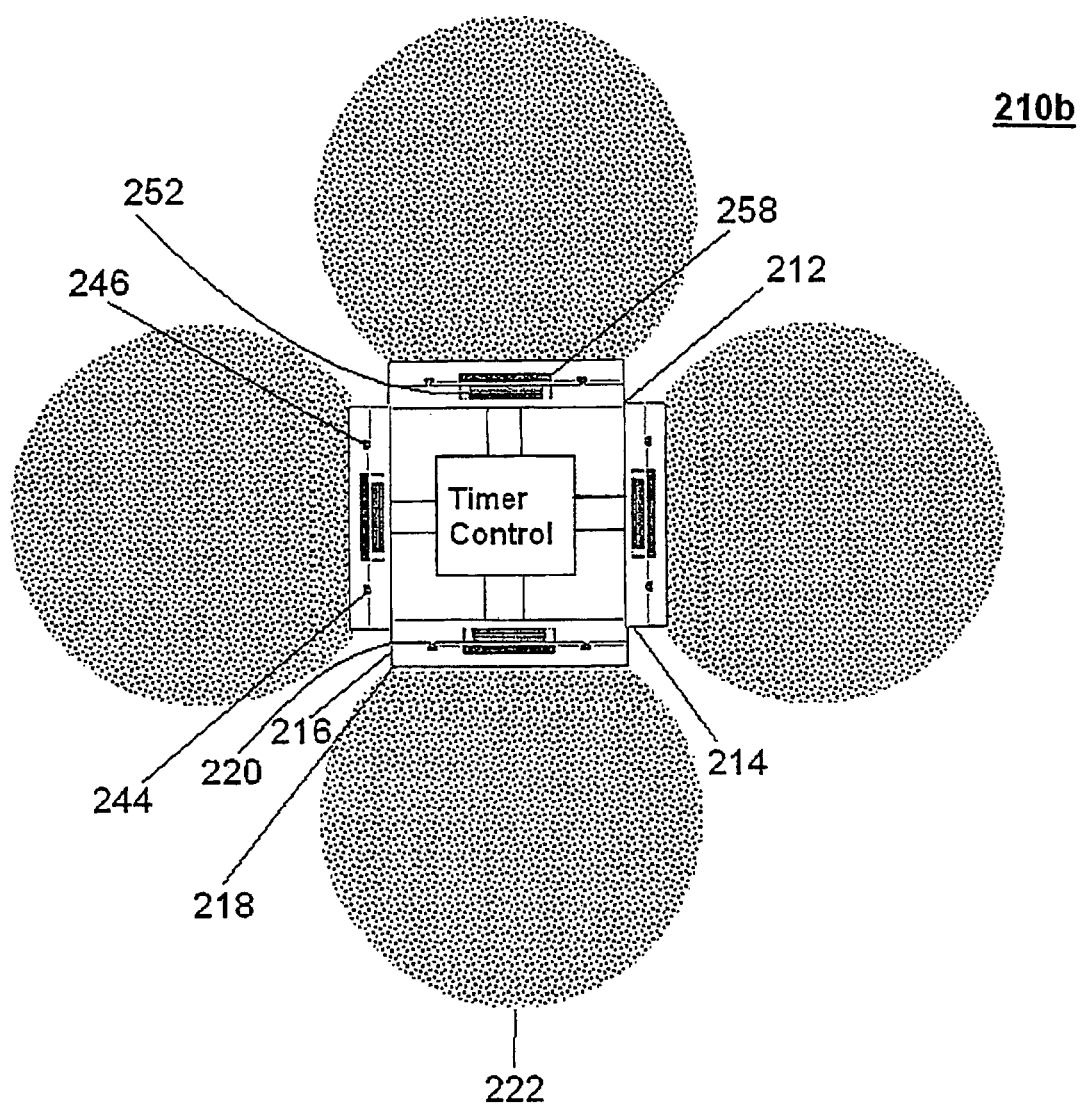
FIG. 9 is a schematic view of another embodiment of a polymer-carrying unit according to the invention.
Figure 10:
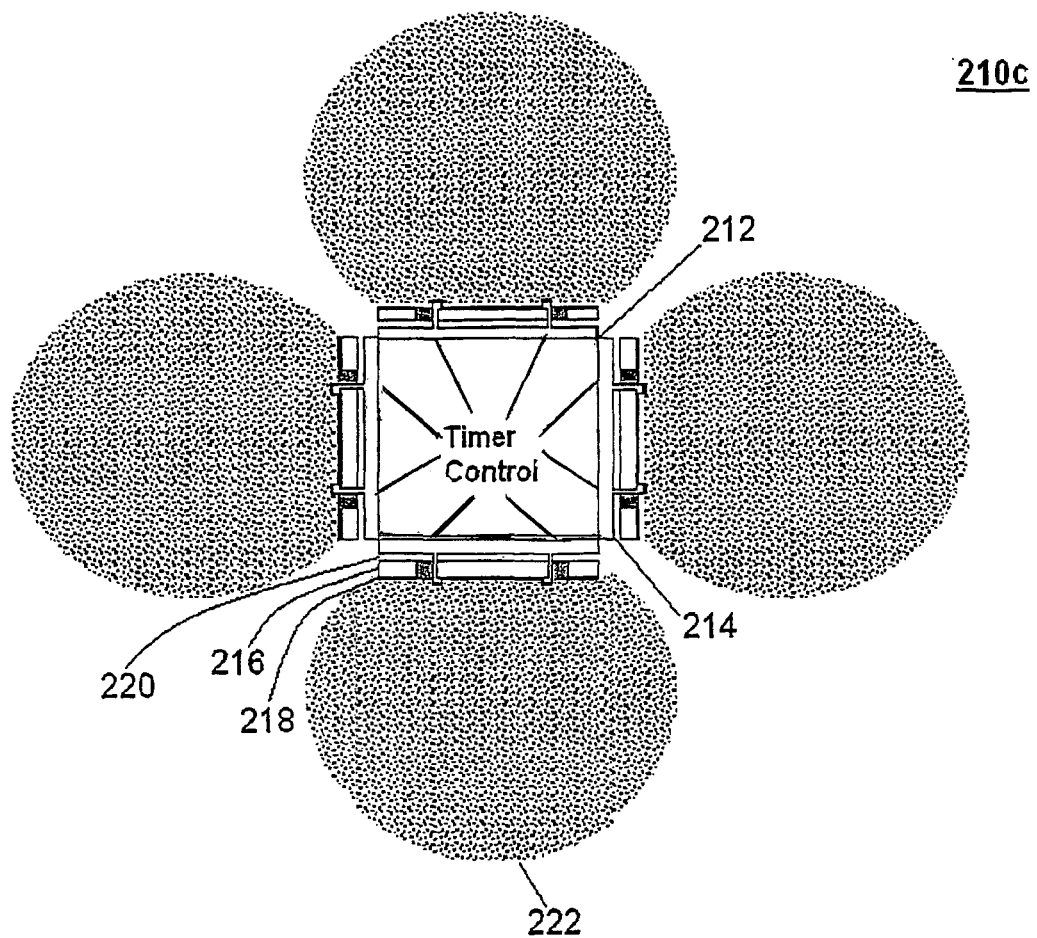
FIG. 10 is a schematic view of another embodiment of a polymer-carrying unit according to the invention.

FIGS. 8, 9, and 10 illustrate, in a schematic view, other embodiments of polymer-carrying units, 210a, 210b and 210c according to this invention, which can be used to facilitate weight loss and to treat obesity, wherein the polymer molecules are releasably coupled to each unit by different coupling means. Accordingly, each unit will have a decoupling means specific for the particular coupling means.

In general, each polymer-carrying unit 210a, 210b, 210c includes a carrier 212 having an outer surface 214, at least one coupling member 216 having a first surface 218 and a second surface 220, a plurality of polymer molecules 222 associated with first surface 218 of coupling member 216, and a coupling means 224 for releasably coupling second surface 220 to outer surface 214. Each unit further comprises a decoupling means for selectively decoupling carrier 212 from coupling member 216, which decoupling means will be discussed in more detail below. Decoupling means can allow for polymer-carrying unit 210a, 210b, 210c to disintegrate and pass through the pylorus after a certain, controllable period of time.

Carrier 212 can be made of a wide variety of different materials, which can include, but are not limited to electrically non-conductive silicon and other biocompatible materials such as composite acrylics. The carrier can adopt a wide variety of different shapes. For example, which is not meant to be limiting, carrier 212 can adopt a sphere-like shape, a triangular-like shape, a pyramid-like shape, or a cube-like shape. Preferably, the carrier comprises internal cavity 272, as shown in FIGS. 8-13, which houses the necessary electronics. The electronics can be insulated and may be further encapsulated within the internal cavity of the carrier using electrically non-conductive silicon and other biocompatible materials such as composite acrylics.

As discussed above for the embodiments shown in FIGS. 1-6, polymer molecules 22 can include any polymer that can expand when in contact with aqueous solutions, and can include, but are not limited to, natural clays (for example, which is not meant to be limiting, Bentonite), microcrystalline hydrogels, polyolefins, polyvinyl alcohol, poly(ethyloxazoline), polyvinylacetate-polyvinylalcohol copolymers, poly(2-hydroxyethylacrylate), poly(2-hydroxyethylmethacrylate), polyacrylic acid, and copolymers thereof, polysaccharides, water soluble proteins, polynucleic acids, or a combination thereof. Moreover, they can be prepared using a variety of different methods, also discussed above.

In the embodiments illustrated in FIGS. 8-10, polymer molecules 22 can be coupled to first surface 218 of coupling member 216 through a variety of different methods. In one embodiment, polymer molecules having high densities can be deposited onto the first surface of the coupling member directly. In another embodiment, the polymer molecules may be coupled to the first surface using glue. The glue may be selected from a wide variety of different glues, which can include, but are not limited to, medical glues such as medical grade cyanoacrylate adhesive. In another embodiment (not shown), the polymer molecules may be inserted into a sac made from a permeable absorbable liner. This liner may be made from a variety of different products, which can include, but are not limited to, medical gauze and the like. The sac may then be attached to the first surface of the coupling member through different ways, including, but not limited to, suturing and/or gluing.

FIGS. 8-13 illustrate that coupling member 216 can be coupled to outer surface 214 in a wide variety of different ways through coupling means 224, which can include, but is not limited to, a frictional force (FIGS. 8, 9, 11, 13, and 14) and piezoelectric hinges (FIGS. 10, 15, and 16), or combinations thereof. Decoupling means, which can be used to decouple coupling member 216 from outer surface 214 can include, but is not limited to, means for producing an electromagnetic force, means for producing electromagnetically-induced vibrations, means for producing piezoelectricity, and various electronic devices, which can include, but are not limited to, timers, microcontrollers, power transistors with high impulse current delivery capabilities, batteries and/or radio-frequency receivers and transmitters. These devices may be used to program the unit to disintegrate after a desired amount of time prior to ingestion or after ingestion. For example, which is not meant to be limiting, radio-frequency receivers can receive a signal from a transmitter and allow for the activation of decoupling means after ingestion of polymer-carrying unit 210a, 210b, 210c. Alternatively, again without limiting, the timer(s) can be pre-programmed to initiate the disintegration of the device after a certain period of time, and without the need for external communication with a transmitter.

Figure 11:
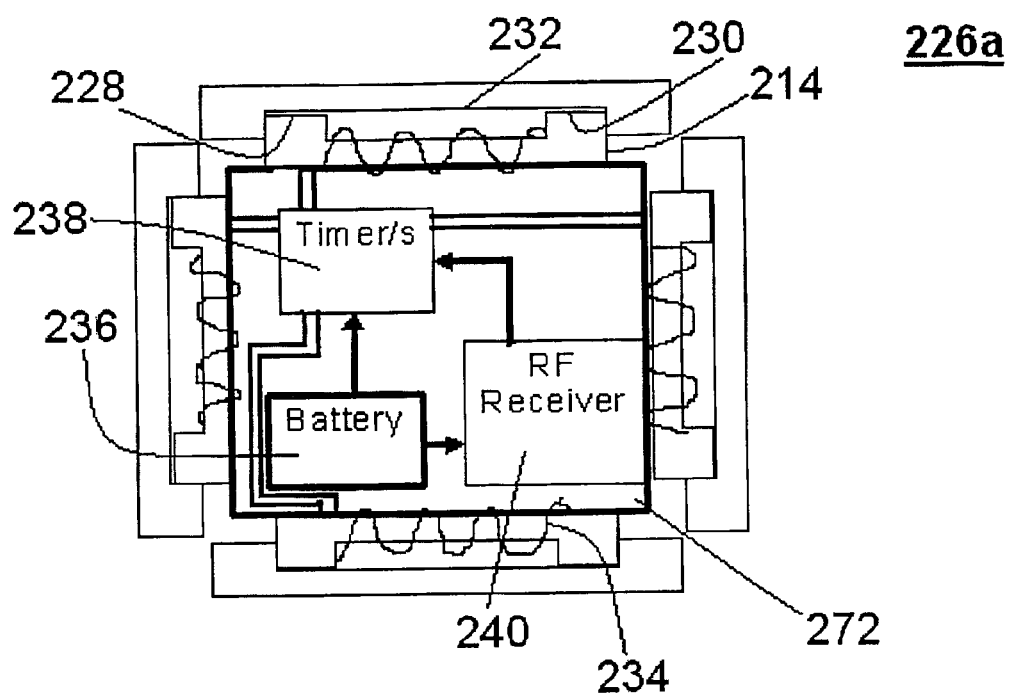
FIG. 11 is a schematic view of one embodiment of a decoupling means according to the invention.
Figure 12:
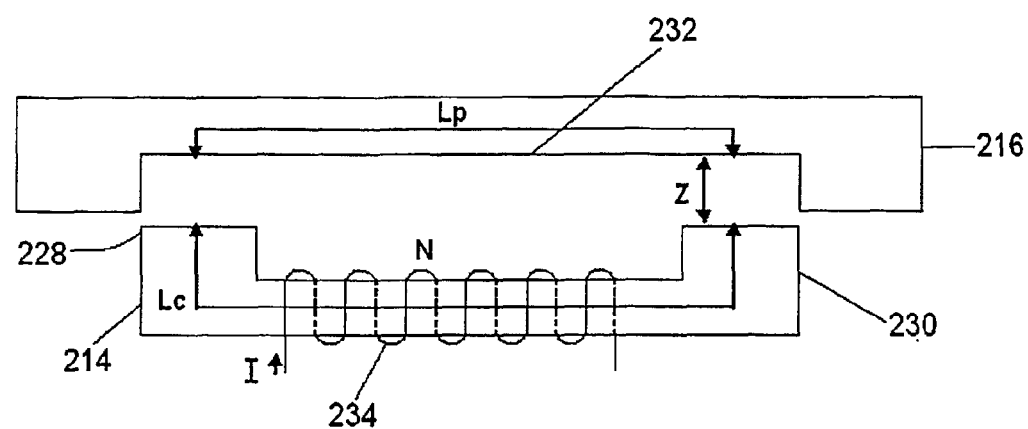
FIG. 12 is an exploded view of a portion of the decoupling means of FIG. 11.

FIGS. 11 and 12 are illustrative of one embodiment of a decoupling means, referred to generally as element numeral 226a, useful with the polymeric-carrying unit as illustrated in FIG. 8. In the unit of FIG. 8, coupling means 224 comprises a frictional force that is created by the outer surface 214 of the carrier tightly meshing with coupling member 216. In order to prevent separation of coupling member 216 to outer surface 214, the frictional force should desirably be of sufficient strength to overcome normal peristaltic movement in the stomach. In one embodiment, the frictional force is set to be at least 2 Newtons. This value may be calculated assuming that a maximum peristaltic pressure of 150 mmHg exerted on a fully expanded polymer on a coupling member 216 having dimensions of 1 cm square is about 1.5 Newtons. Of course, this value may be different depending on the dimensions of coupling member 216. As shown in FIG. 11, outer surface 214 includes at least two projections 228 and 230, which can engage indent 232 of coupling member 216 and can create a sufficiently strong mechanical frictional force.

To break the frictional force holding coupling member 216 to outer surface 214, an electromagnet can be used as decoupling means 226a, as illustrated in FIGS. 11 and 12. As shown in FIGS. 11 and 12, a wire 234 is wrapped around the outer surface 214 of carrier 212. Coupling member 216 can be made of a biocompatible material with high magnetic permeability, AISI Type 316L Stainless Steel. Outer surface 214 and coupling member 216 can be repelled from one another by inducing an electrical current through wire 234 surrounding outer surface 214. In one embodiment, this electrical current is set to be strong enough so that the resulting magneto-motive force overcomes coupling means 224 (i.e., the frictional forces keeping outer surface 214 and coupling member 216 together).

As shown in FIG. 12, the electromagnet can include N turns of wire 234 carrying a current I around a core of outer surface 214 of cross-sectional area S and constant permeability $\mu_c$. The repelling force exerted on coupling member 216, assuming that the member has permeability $\mu_b$ and cross-section $S_b$, can be calculated as follows. It should be noted that the following calculation assumes that a gap is present between coupling member 216 and outer surface 214 (as shown in FIGS. 8, 11 and 12), and that this gap has the same cross-sectional area as outer surface 214 (see FIG. 12).

If it is assumed that coupling member 216 is slightly separated from outer surface 214 by an air gap of width Z, the magnetic flux $\phi$ passing through the core and the gap can be obtained as a magnetic voltage drop around the entire magnetic circuit, which subsequently can be related to the magneto-motive force produced by the electromagnet. $\phi$ is expressed as:

$$\phi = NI/(Rc + Rb + 2Rg)$$

where $Rc = Lc/(\mu_c * S)$, $Rb = Lb/(\mu_b * Sb)$ and $Rg = z/(\mu_0 * S)$ are the reluctances of the core of outer surface 214, coupling member 216 and the air gap, respectively. The repelling force, Fm, acting on coupling member 216 can be expressed as:

$$Fm = -(\phi^2)/(\mu_0 * S)$$

Since the magnetic permeabilities of outer surface 214 and coupling member 216 are much larger than $\mu_0$, the equivalent reluctance can be mainly dominated by the air gaps reluctance. Lengths Lc and Lb can be set to 1 cm, and S and Sb can be sections of 1 mm×1 cm.

The force required to repel coupling member 216 should be larger than the mechanical friction holding the member to outer surface 214 (which can be estimated to be 2 Newtons). If such a repelling force is needed for a 0.25 mm gap between outer surface 214 and coupling member 216, 100 windings of the electromagnet would be required for a 1A impulse current.

As discussed above, decoupling means 226a can be activated after a certain amount of time has passed. FIG. 11 illustrates that decoupling means 226a, including the electromagnet discussed above, can be activated through a plurality of electronic devices. In this embodiment, carrier 12 has an internal cavity 272 for housing these electronic devices. These electronic devices can include, but are not limited to, a timer 236, a battery 238, and/or a radio-frequency (RF) receiver 240. As shown in FIG. 11, timer 236, battery 238 and RF receiver 240 are all electronically connected. Further, timer 236 can be connected to outer surface 214, which has wire 234 wrapped around it, through wires 242 to allow for controlled repulsion of coupling member 216 from outer surface 214. To protect the electronic devices, it may be desirable to cover each device with an insulating material, such as nylon or silicon. In one embodiment, the insulating material is oxide.

In one embodiment (not shown), separate electronic devices can be used to control the decoupling of each coupling member from the carrier of the polymer-carrying unit. By having a separate electronic timing control, different disintegration patterns can be used. For instance, a separation to two parts consisting of Y/2 units might occur after 2 hours, a separation to 4 smaller parts consisting of Y/4 units might occur after 3 hours, etc.

In the polymeric-carrying unit embodiment shown in FIG. 9, coupling means 224 includes frictional force. It is understood that the frictional force must be of sufficient strength to prevent separation of coupling member 216 from outer surface 214. In this embodiment, outer surface 214 can further include at least two pegs 244 and 246, which can engage indents 248 and 250, respectively, of coupling member 216 and thus create a sufficiently strong mechanical frictional force.

Figure 14:
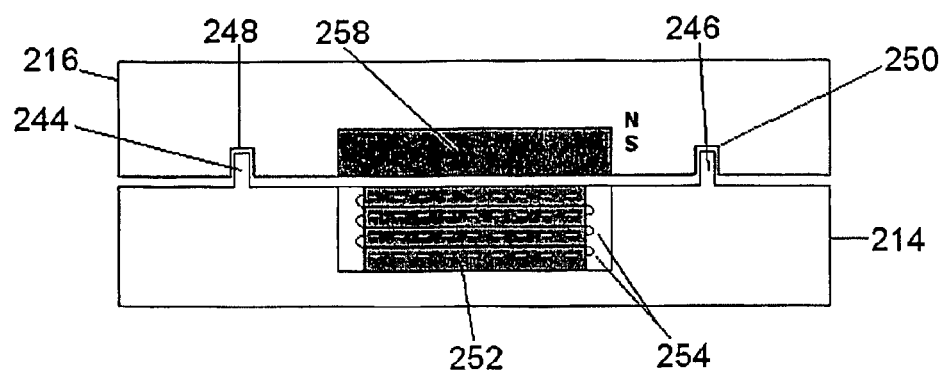
FIG. 14 is an exploded view of a portion of the decoupling means of FIG. 13.

To break the frictional force holding coupling member 216 to outer surface 214, an electromagnet is used in decoupling means, the decoupling means referred to generally as element numeral 226b, as illustrated in FIGS. 13 and 14. As illustrated in FIGS. 13 and 14, an electromagnet 252 can be embedded within outer surface 214. Electromagnet 252 can be formed by wrapping a wire 254 around a ferromagnetic core 256 in multiple windings, while coupling member 216 can embed at least one biocompatible permanent magnet 258, for example bonded Neodymium Iron Boron.

In this embodiment of decoupling means 226b, outer surface 214 and coupling member 216 can be repelled from one another by inducing vibrations due to the magnetic interaction between permanent magnet 258 embedded in coupling member 216 and electromagnet 252 embedded in outer surface 214. Specifically, an alternating electrical current flowing through wire 254 of electromagnet 252 can cause the poles of the electromagnet to alternate, thus repelling or attracting coupling member 216 to outer surface 214 until these vibrations become strong enough so that the friction force holding them together is overcome. It may be desirable that this electrical current be sufficiently strong to ensure that the resulting magneto-motive force can introduce sufficiently strong vibrations to overcome coupling means 224.

As shown in FIG. 14, electromagnet 252 can consist of N windings of single-loop wire 254 with a winding radius of r, carrying an alternating current I around a core of cross-sectional area S and constant permeability $\mu_c$. Assuming permanent magnet 258 embedded in coupling member 216 is made from bonded Neodimium Iron Boron of dimensions 0.5×0.5 cm, giving a magnetic field Bo=0.7 T, and electromagnet 252 embedded in outer surface 214 has similar dimensions with 10 to 20 windings, then the magnetic field produced by the electromagnet $Bi=\mu_c$ NI/2r can also reach the same value, which for convenience will be labeled with B. Consequently, outer surface 214 and coupling member 216 can be subjected to dynamic attraction and repulsion changing with the alternating current controlling electromagnet 252. Thus, vibrations can be introduced with maximum repelling and attracting force of F=I.r.B.

As discussed above for decoupling means 226a, decoupling means 226b can also be controlled through a variety of electronic devices such as timer 236, battery 238 and/or RF receiver 240. Moreover, the electronic devices can allow selective disintegration of polymer-carrying unit 210, by uncoupling coupling member 216 from outer surface 214 only at certain, specific locations on the unit.

In the embodiment shown in FIG. 10, coupling means 224a includes piezoelectric hinges 260, while decoupling means includes electrodes which produce an electric voltage. Piezoelectric hinges 260 can be used to couple coupling member 216 to outer surface 214, and are hingedly connected to outer surface 214. The piezoelectric hinges can be made of a zinc oxide-based biocompatible piezoelectric material, for example one produced by Gredmann, San Jose, Calif. In one embodiment, piezoelectric hinges 260 can have dimensions of about 2 to about 3 mm in height, and about 0.2 to about 0.5 mm in width. In one embodiment, piezoelectric hinges 260 can adopt a general "T"-like conformation.

Figure 15:
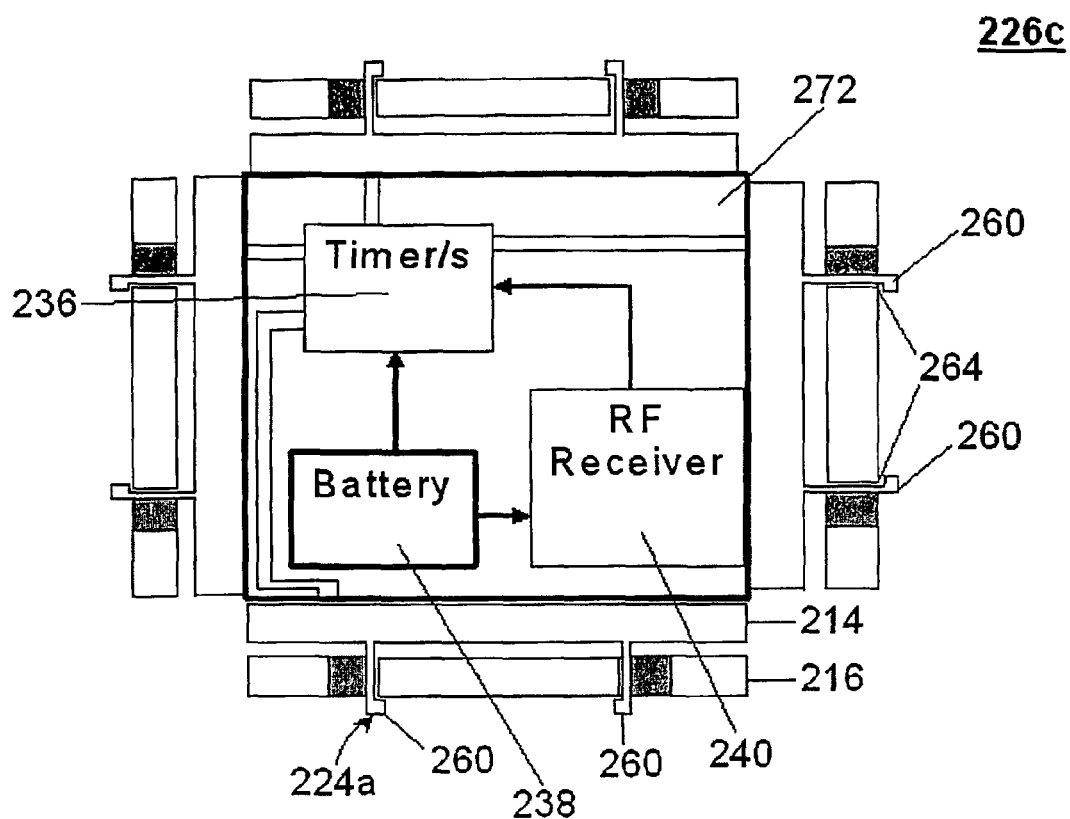
FIG. 15 is a schematic view of one embodiment of a decoupling means according to the invention.
Figure 16:
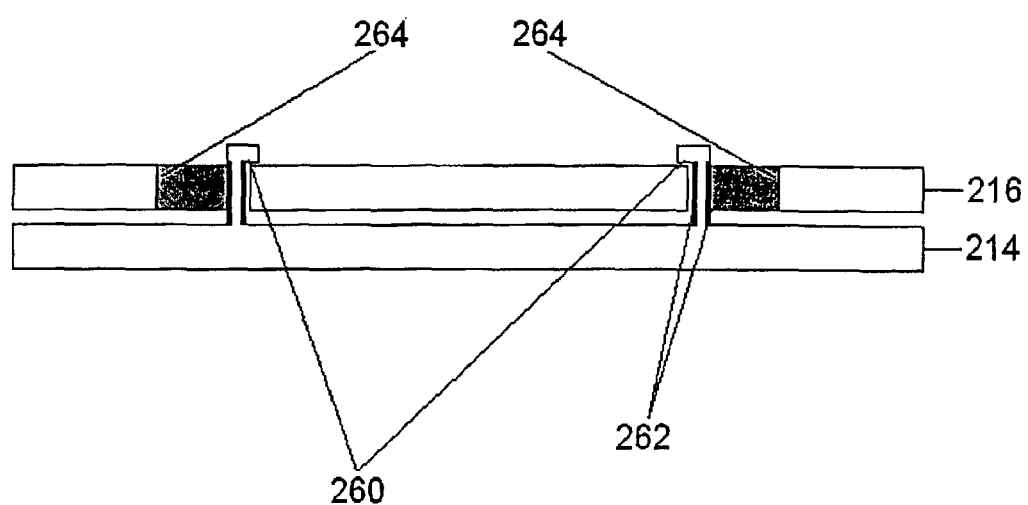
FIG. 16 is an exploded view of a portion of the decoupling means of FIG. 15.

As shown in more detail in FIGS. 15 and 16, coupling member 216 includes a plurality of apertures 264 through which piezoelectric hinges 260 can be inserted to couple coupling member 216 to outer surface 214. As discussed above, it may be desirable that piezoelectric hinges 260 exert a holding force sufficiently greater than the maximal peristaltic force in the stomach to prevent decoupling of coupling member 216 and outer surface 214.

To displace piezoelectric hinges from a coupling position, to an uncoupling position in apertures 264, an electric voltage can be applied through electrodes 262 of the decoupling device shown in FIG. 16, referred to generally as element numeral 226c. In one embodiment, by applying electric voltage to piezoelectric hinges 260, a displacement ranging between 10 to 20% from the coupling position to the uncoupling position can be produced, which can allow for the piezoelectric hinges to detach from coupling member 216 and exit through apertures 264 in coupling member 216. In the uncoupling position, piezoelectric hinges 260 can no longer engage and retain coupling member 216, which can be released from outer surface 214.

Decoupling means 226c useful in the embodiment illustrated in FIG. 10, can be controlled through a variety of electronic devices such as timer 236, battery 238 and/or RF receiver 240, as shown in FIGS. 10 and 15. Moreover, the electronic devices can allow selective disintegration of polymer-carrying unit 210, by uncoupling coupling member 216 from outer surface 214 only at certain, specific locations on the unit.

Figure 17:
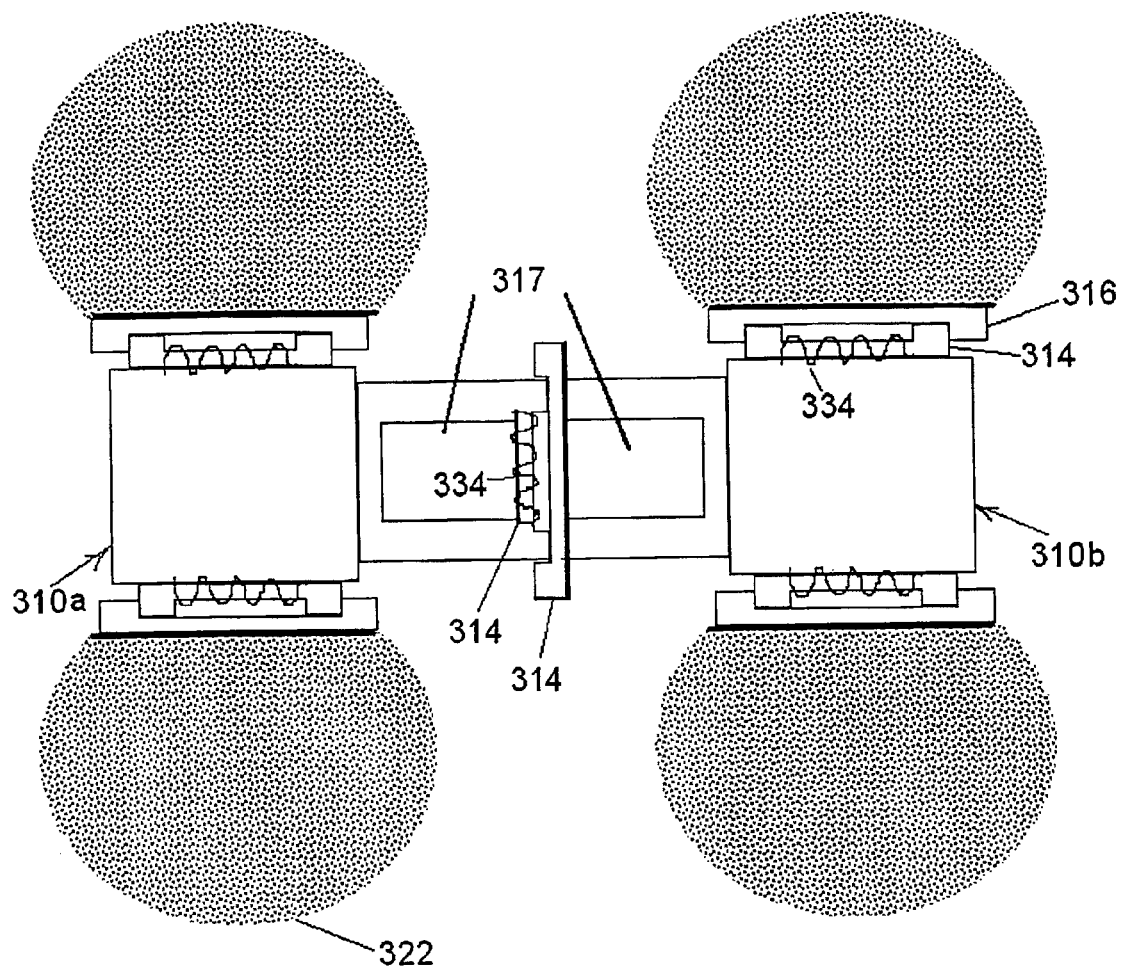
FIG. 17 is a schematic view of one embodiment of an arrangement of polymer-carrying units according to the invention.
Figure 19:
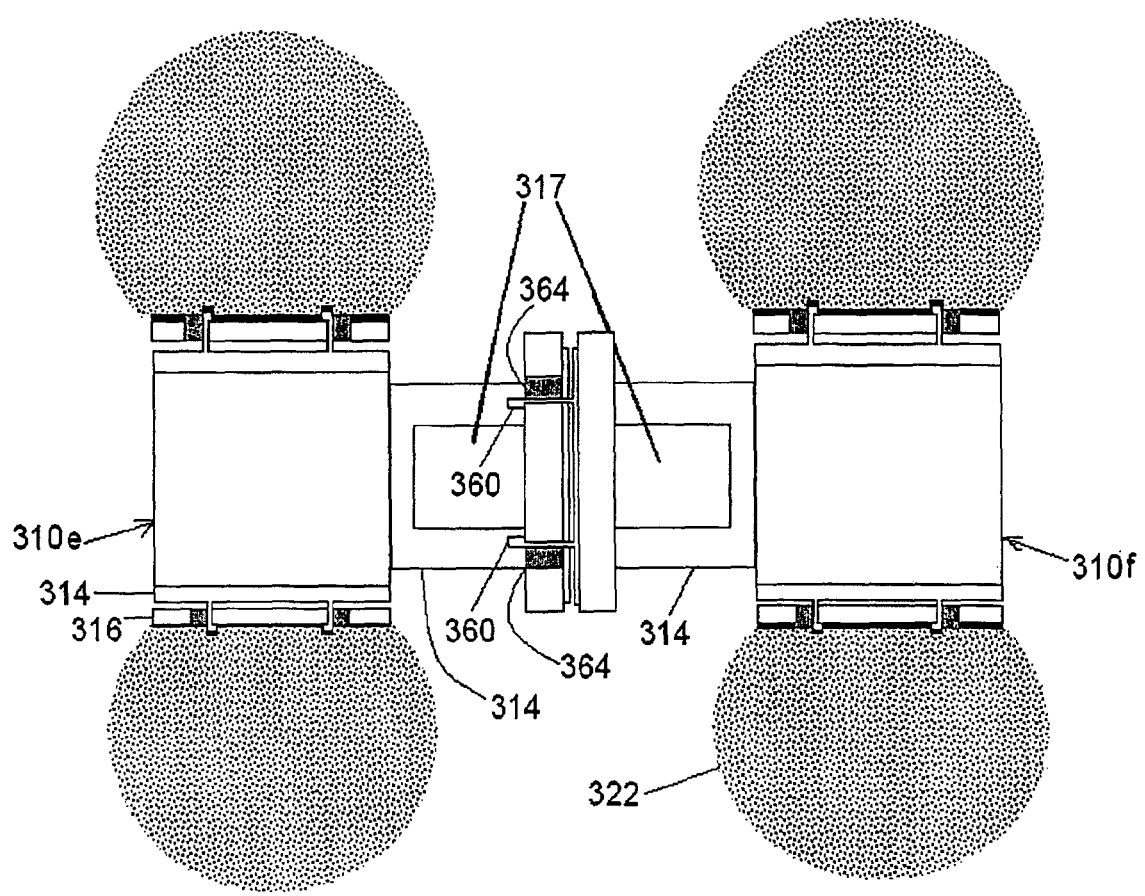
FIG. 19 is a schematic view of one embodiment of an arrangement of polymer-carrying units according to the invention.

FIGS. 17-19 illustrate further embodiments according to the invention. In these embodiments, a plurality of polymer-carrying units can be interconnected to form an arrangement. In the embodiment illustrated in FIG. 17, one of the outer surfaces 314 of polymer-carrying unit 310a is extended by means of a spacer 317 and has a wire 334 operably attached at its extremity. Another polymer-carrying unit 310b also has an extended outer surface 314, which is extended by means of spacer 317 and is adapted to frictionally receive the extended outer surface of polymer-carrying unit 310a as described above. Decoupling means can be used to decouple the polymer-carrying units as described above. Moreover, as discussed above, decoupling means dedicated only to the decoupling of one unit from another may be used to allow for partial disintegration of the arrangement.

In the embodiment shown in FIG. 18, outer surface 314 of polymer-carrying unit 310c is extended by means of a spacer 317. Outer surface 314 can include electromagnet 352 embedded at its extremity. Outer surface 314 of polymer-carrying unit 310d is also extended by means of spacer 317 and the outer surface extremity includes a biocompatible permanent magnet 358 embedded therein. Outer surface 314 of polymer-carrying unit 310c further includes pegs 344 and 346, which are frictionally received by the outer surface of polymer-carrying unit 310d, as described above. Decoupling means can be used to decouple the polymer-carrying units, as described above. Moreover, as discussed above, decoupling means dedicated only to the decoupling of one unit from another may be used to allow for partial disintegration of the arrangement.

In the embodiment illustrated in FIG. 19, one of the outer surfaces 314 of polymer unit 310f can be extended by means of a spacer 317, and can include piezoelectric hinges 360. One of the outer surface 314 of polymer-carrying unit 310e can also be extended by a spacer 317 and can include apertures 364 for receiving the hinges, as described above. Decoupling means can be used to decouple the units as described above. Moreover, as described above, decoupling means dedicated only to the decoupling of one unit from another may be used to allow for partial disintegration of the arrangement.

It may be desirable to include spacers 317 within polymer-carrying unit 10 in order to allow for the addition of various active agents. Active agents may be selected from the group consisting of enzymatic agents, medicinal agents, chemical agents, or combinations thereof. For example, which is not meant to be limiting, it may be desirable to deliver various pharmaceutical agents that also facilitate weight loss, or enzymes that may accelerate degradation of polymer molecules 322. However, the active agents can also be added to sacs 376, or associated with polymer molecules 322.

According to another embodiment of this invention, there is provided an orally-administrable pharmaceutical dosage form including at least one polymer-carrying unit and, if desired, a pharmaceutically acceptable excipient such as binders, fillers and disintegrants, for example, starch. The pharmaceutical dosage form may take various forms, which include, but are not limited to, liquids, soft substances, powder-like substances, and hard pharmaceutical substances such as soft capsules, hard capsules and tablets. In one embodiment, the pharmaceutical dosage form is a capsule. In another embodiment, the capsule can be coated with a pH-sensitive coating. The pH-sensitive coating may prevent dissolution until the stomach reached, to prevent contact between polymer molecules 22 and aqueous solutions.

The administration of a polymer-carrying unit or a dosage form including at least one polymer-carrying unit can be used as a non-invasive technique for the reduction of gastric volume. The unit or a dosage form including at least one unit can be administered by mouth, where it will reach the stomach. Once in the stomach, the polymer molecules can be contacted with aqueous solutions, which will result in their expansion. The expanded polymer molecules, which cannot pass through the pylorus, can fill a significant portion of the volume of the stomach, resulting in the attainment of a feeling of satiety. After a desired period of time has passed, polymer molecules can be selectively decoupled from the unit, or portions of the dosage form can be selectively decoupled from one another, in order for the decoupled portions to exit the stomach through normal peristaltic movement.

While the invention has been described in conjunction with the disclosed embodiments, it will be understood that the invention is not intended to be limited to these embodiments. On the contrary, the current protection is intended to cover alternatives, modifications and equivalents, which may be included within the spirit and scope of the invention. Various modifications will remain readily apparent to those skilled in the art.

What is claimed is:

1. An orally administrate polymer-carrying unit for expanding in a stomach of a mammal to fill a space in the stomach and deliver at least one active agent thereto, the polymer-carrying unit comprising:
   (a) a carrier having an outer surface, an inner surface, and an internal cavity formed by the inner surface;
   (b) at least one coupling member disposed externally of the carrier and having a first surface facing away from the carrier and a second surface facing toward the carrier;
   (c) a plurality of polymer molecules, expandable in the presence of an aqueous solution, coupled to the first surface of the coupling member;
   (d) a coupler releasably coupling the second surface of the coupling member to the outer surface of the carrier; and
   (e) a decoupler comprising an electronic device housed within the internal cavity of the carrier and arranged for selectively decoupling the coupling member from the carrier; and
   (f) an active agent releasably associated with the carrier, the coupling member, the polymer molecules, or a combination thereof.

2. The polymer-carrying unit as claimed in claim 1, the carrier having a sphere-like shape.

3. The polymer-carrying unit as claimed in claim 1, the carrier having a triangular-like or pyramid-like internal shape.

4. The polymer-carrying unit as claimed in claim 1, the carrier having a cube-like shape.

5. The polymer-carrying unit as claimed in claim 1, wherein the coupler is selected from the group consisting of means for producing an electromagnetic force, means for producing a frictional force, piezoelectric hinges, or combinations thereof.

6. The polymer-carrying unit as claimed in claim 1, wherein the electronic device of the decoupler is selected from the group consisting of a timer, a battery, a radio-frequency receiver, or combinations thereof.

7. The polymer-carrying unit as claimed in claim 1, wherein the coupler comprises means for producing a frictional force and the decoupler comprises an electromagnet operatively associated with the outer surface of the carrier and means for activating the electromagnet to create a magnetic field.

8. The polymer-carrying unit as claimed in claim 7, wherein the coupling member comprises a material that can be repelled by the magnetic field.

9. The polymer-carrying unit as claimed in claim 1, wherein the coupler is at least one piezoelectric hinge and the decoupler is arranged to produce an electric voltage.

10. The polymer-carrying unit as claimed in claim 1, wherein the polymer molecules are a mixture of natural clay and a biocompatible polymer.

11. The polymer-carrying unit as claimed in claim 1, wherein the polymer molecules are biodegradable.

12. The polymer-carrying unit as claimed in claim 1, wherein the active agent is selected from the group consisting of enzymatic agents, medicinal agent, chemical agents, or combinations thereof.

13. An arrangement of polymer-carrying units as claimed in claim 1, the arrangement comprising a first unit and a second unit, wherein the outer surface of the first unit is releasably coupled to the outer surface of the second unit by means of electric forces, magnetic forces, electrostatic forces, electromagnetic forces, or a combination thereof.

14. A orally administrable dosage form, the dosage form comprising:
   (a) one or more polymer-carrying units each comprising:
      (i) a carrier having an outer surface, an inner surface, and an internal cavity formed by the inner surface;
      (ii) at least one coupling member disposed externally of the carrier and having a first surface facing away from the carrier and a second surface facing toward the carrier;
      (iii) a plurality of polymer molecules, expandable in the presence of an aqueous solution, coupled to the first surface of the coupling member;
      (iv) a coupler releasably coupling the second surface of the coupling member to the outer surface of the carrier; and
      (v) a decoupler comprising an electronic device housed within the internal cavity of the carrier and arranged for selectively decoupling the coupling member from the carrier; and
   (b) at least one pharmaceutically acceptable excipient.

15. The orally administrable dosage form of claim 14, wherein the dosage form is a capsule.

16. The orally administrable dosage form of claim 15, wherein the capsule is coated with a pH-sensitive coating layer.

17. The orally administrable dosage form of claim 13, wherein the coating layer is arranged to dissolve in gastric juice.

* * * * *